US006518252B2

(12) United States Patent
Wooley et al.

(10) Patent No.: US 6,518,252 B2
(45) Date of Patent: Feb. 11, 2003

(54) METHOD OF TREATING AQUATIC ANIMALS WITH AN ANTIMICROBIAL AGENT AND CHELATING AGENT

(75) Inventors: Richard E. Wooley, Athens, GA (US); Branson W. Ritchie, Athens, GA (US); Victoria V. Burnley, Bogart, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 09/954,965

(22) Filed: Sep. 18, 2001

(65) Prior Publication Data

US 2002/0098208 A1 Jul. 25, 2002

Related U.S. Application Data

(60) Provisional application No. 60/234,374, filed on Sep. 20, 2000.

(51) Int. Cl.[7] ......................... A61K 31/70; A61K 38/16; A61K 31/65; A61K 31/43
(52) U.S. Cl. ............................. 514/29; 514/6; 514/31; 514/34; 514/37; 514/152; 514/192
(58) Field of Search ......................... 514/29, 34, 37, 514/6, 31, 192, 152

(56) References Cited

U.S. PATENT DOCUMENTS

| | | | | |
|---|---|---|---|---|
| 4,122,158 | A | 10/1978 | Schmitt | 424/27 |
| 5,098,417 | A | 3/1992 | Yamazaki et al. | 604/304 |
| 5,364,638 | A | 11/1994 | Sugo | 424/78.17 |
| 5,455,266 | A | * 10/1995 | Kusuda et al. | 514/450 |
| 5,688,516 | A | 11/1997 | Raad et al. | 424/409 |
| 5,942,232 | A | * 8/1999 | Costa | 424/195.1 |

OTHER PUBLICATIONS

Alekshun, M.N. & Levy, S.B. Regulation of Chromosomally mediated Multiple Antibiotic Resistance: The mar Regulon. *Antimicrob. Agents & Chemotherapy* 41, 2067–2075 (1997).
Ashworth, C. D. & Nelson D. R.. Antimicrob. Potentiation of Irrigation Solutions Containing Tris–(hydroxymethyl) aminomethane–EDTA. *J. Am. Vet. Med. Assoc. 197*, 1513–1514. (1990).
Bayer, M. E. & Leive L. Effect of Ethlyenediamintetraacetate Upon the Surface of *Escherichia coli*. *J. Bacteriol. 130*, (1364–1381. 1977).
Bjorling, D. E. &. Wooley R. E. EDTA–Tromethamine Lavage as an Adjunct Treatment for Multiple Fistulas in a Dog. *J. Am. Vet. Med. Assoc. 181*, 596–597. (1982).
Blue, J. L., Wooley R. E. & Eagon, R. G. Treatment of Experimentally Induced *Pseudomonas aeruginosa* Otitis Externa in the Dog by Lavage with EDTA–Tromethamine Lysozyme. *Am. J. Vet. Res. 35*, 1221–1223. (1974).
Brown, M. R. W. & Richards, M. E. Effect of Ethylenediaminetetraacetate on the resistance of *Pseudomonas aeruginosa* to antibacterial agents. *Nature (London). 207*, 1391–1393. (1965).

Farca, A. M., Nebbia, P. & Re, G. Potentiation of the In Vitro Activity of Some Antimicrobial Agents against Selected Gram–Negative Bacteria by EDTA–Tromethamine. *Vet. Res. Comm. 17*, 77–84. (1993).
Gerberick, G. F. & Castric, P. A. In vitro Susceptibility of *Pseudomonas aeruginosa* to Carbenicillin, Glycine, and Ethylenediaminetetraacetic Acid Combinations. *Antimicrob. Agents & Chemotherapy. 17*, 732–735. (1980).
Goldschmidt, M. C., Kuhn, C. R., Perry, K. & Johnson, D. E. EDTA and Lysozyme Lavage in the Treatment of Pseudomonas and Coliform Bladder Infections. *J. Urol. 107*, 969–972. (1972).
Goldschmidt, M. C. & Wyse, O. The role of Tris in EDTA Toxicity and Lysozyme Lysis. *J. Gen. Microbiol. 47*, 421–431 (1967).
Kreig, D.P., Bass, .A. & Mattingly, S.J. Phosphorylcholine stimulates Capsule Formation of Phosphate–Limited Mucoid *Pseudomonas aeruginosa. Infect. Immun. 56*, 864–873 1988).
Leive, L. A Nonspecific Increase in Permeability in *Escherichia coli* Produced by EDTA. *Proc. Nat. Acad. Sci. USA.53*, 745–750 (1968).
Leive, L., Shovlin, V. K. & Mergenhagen, S. E. Physical, Chemical, and Immunological Properties of Lipopolysaccharide Released from *Escherichia coli* by Ethylenediaminetetraacetate. *Biol. Chem. 243*, 6384–6391 (1968).
Monkhouse, D. C. & Graves, G. A. The Effect of EDTA on the Resistance of *Pseudomonas aeruginosa* to Benzalkonium, Chloride. *Aust. J. Pharm. 48*, 570–575 (1967).
Roberts, N. A., Gray, G. W. & Wilkinson, S. C. The Bactericidal Action of Ethylenediamine–tetra–acetlc Acid on *Pseudomonas aeruginosa. Microbios 7–8*, 189–208. (1970).
Russel, A. D. Effect of Magnesium Ions & Ethylenediaminetetraacetic acid on the Activity of Vancomycin against *Escherichia coli* and *Staphylococcus aureus*. *J. Appl. Bacteriol. 30*, 395–401 (1967).

(List continued on next page.)

*Primary Examiner*—Kevin E. Weddington
(74) *Attorney, Agent, or Firm*—Womble Carlyle Sandridge & Rice, LLP

(57) ABSTRACT

The present invention relates to novel method of reducing microbial infections, especially bacterial infections, of animals, especially of aquatic animals such as fish maintained in tanks or aquaria. The present invention provides bathing and dipping methods for reducing a microbial infection of an animal with an antibiotic solution of enhanced antimicrobial activity comprising at least one chelating agent and at least one antibiotic effective against the microbial infection. The present invention also provides a method for reducing a microbial infection of an animal comprising bathing or dipping an animal having a microbial infection in an antimicrobial solution comprising the chelating agent EDTA, and at least one antibiotic, and optionally a pH buffering agent. The immersion of the aquatic animal in the antimicrobial solution containing the EDTA, antibiotic and pH buffering agent may be repeated until the microbial burden of the animal is eliminated. The present invention further provides kits for use in administering an enhanced activity antibiotic solution.

35 Claims, 6 Drawing Sheets

OTHER PUBLICATIONS

Sabath, L. D. Synergy of Antibacterial Substances by Apparently Known Mechanisms. *Antimicrob. Agents & Chemotherapy.* 210–217 (1967).

Sparks, T. A., Kemp, D. T., Wooley, R. E. & Gibbs, P. S. Antimicrobial Effect of Combinations of EDTA–Tris and Amikacin or Neomycin on the Microorganisms Associated with Otitis Externa in Dogs. *Vet. Res. Comm.* 18, 241–249 (1994).

Wooley, R. E., Berman, A. P. & Shotts Jr, E. B. Antibiotic–Tromethamine–EDTA Lavage for the Treatment of Bacterial Rhinitis in a Dog. *J. Am. Vet. Med. Assoc.* 75, 817–818 (1979).

Wooley, R. E. & Blue, J. L. In Vitro Effect of EDTA–Tris–Lysozyme Solutions on Selected Pathogenic Bacteria. *J. Med. Microbiol.* 8, 189–194 (1974).

Wooley, R. E., Blue, J. L., Scott, T. A. & Belcher, M K. Attempt to Induce *Pseudomonas pyoderma* in the Dog. *Am. J. Vet. Res.* 35, 807–810 (1974).

Wooley, R. E., Dickerson, H. W., Siramens, K. W., Shotts Jr., E. B. & Brown, J. Effect of EDTA–Tris on an *Escherichia coli* Isolate Containing R Plasmids. *Vet. Microbiol.* 12, 65–75 (1986).

Wooley, R. E. & Jones, M. S. Action of EDTA–Tris and Antimicrobial Agent Combinations on Selected Pathogenic Bacteria. *Vet. Microbiol.* 8, 271–280 (1983).

Wooley, R. E., Jones, M. S. & Shotts Jr., E. B. Uptake of Antibiotics in Gram–negative Bacteria Exposed to EDTA–Tris. *Vet. Microbiol.* 10, 57–70 (1984).

Wooley, R. E., Jones, M. S., Gilbert, J. P. & Shotts Jr., E. B. In Vitro Action of Combinations of Antimicrobial Agents and EDTA–Tromethamine on *Escherichia coli. Am. J. Vet. Res.* 44, 1154–1158 (1983a).

Wooley, R. E., Jones, M. S., Gilbert, J. P. & Shotts Jr., E. B. In Vitro of Combinations of Antimicrobial Agents with EDTA–Tromethamine on *Proteus vulgaris* of Canine Origin. *Am. J. Vet. Res.* 45, 1451–1454 (1984).

Wooley, R. E., Jones, M. S., Gilbert J. P., & Shotts Jr., E. B. In Vitro Action of Combinations of Antibicrobial Agents and EDTA–Tromethamine on *Pseudomonas aeruginosa. Am J. Vet. Res.* 44, 1521–1524 (1983b).

Wooley, R. E., Jones, M. S., Gilbert J. P., & Shotts Jr., E. B. In Vitro Effect of Combinations of Antimicrobial Agents and EDTA–Thromethamine on certain gram–positive Bacteria. *Am. J. Vet. Res.* 44, 2167–2169 (1983c).

Wooley, R. E., Schall, W. D., Eagon, R. G. & Scott, A. A. S. Efficacy of EDTA–Tris–Lysozyme Lavage in the Treatment of Experimentally Induced *Pseudomonas aeruginosa* Cystitis in the Dog. *Am. J. Vet. Res.* 35, 27–29 (1974).

Youngquist, R.S. *Pseudomonas metritis* in a mare. *Vet. Med./Small An. Clinician* 70, 340–342 (1975).

Wooley, R.E., Sander, J. E., Maurer, J.J., Gibbs, P.S. In Vitro Effect of Ethylenediaminetetraacetic Acid–Tris on the Efficacy of Hatchery Disinfectants. *Avian Diseases* 44, 901–906 (2000).

Wooley, R. E., Blue, J.L., Campbell, L.M., Attempted Reversal of Oxytetracycline Resistance of *Proteus mirabilis* by EDTA–Tromethamine Lavage in Experimentally Induced Canine and Feline Cystitis, *Am. J. Vet. Res.* 36, 1533–1535 (1975).

Wooley, R. E., Gilbert, J.P., Shotts, Jr., E.B., Inhibitory Effects of Combinations of Oxytetracycline, Dimethyl Sulfoxide, and EDTA–Tromethamine on *Escherichia coli. Am. J. Vet. Res.* 42, 2010–2013(1981).

* cited by examiner

METHOD OF TREATING AQUATIC ANIMALS WITH AN ANTIMICROBIAL AGENT AND CHELATING AGENT

The present application claims the benefit of U.S. application Ser. No. 60/234,374 filed Sep. 20, 2000, which is incorporated herein by reference.

FIELD OF THE INVENTION

The present invention relates generally to methods of treatment of microbial infections of animals, including aquatic animals and fish. The present invention also relates to kits for the application of the method of administering an effective antimicrobial agent to the external surface of an animal.

BACKGROUND OF THE INVENTION

Aquatic animals are regularly exposed to a medium with a high microbial population. Although the animals have physical and immune system barriers that resist opportunistic infections, such defenses are occasionally breached and an infection results. In the natural environment, the infected animal will overcome the disease and survive, or it will succumb, weaken and die. Since naturally aquatic animals are in limited physical contact with one another, or the water in which they live circulates freely, cross-infection and epidemics are rare unless the water is heavily polluted and/or the animal population is at high density. In the confines of a small aquarium or pond, with ornamental fish or the much larger tanks of fish farming (aquaculture) operations, the possibility of a microbial infection of an entire population is greater. The fish farming, or aquaculture, industry is particularly susceptible to infections of a stock population and the economic consequences of a disease ravaging a tank of fish can be significant. The rapid and effective treatment of a microbial infection, therefore, is essential to save individual fish, and to prevent the spread of disease to healthy animals.

Fish confined to tanks, especially under the high-density conditions prevalent in aquaculture, are sensitive to stress-induced illness. Fish health maintenance for the keeping of ornamental or tropical fish or for the rearing of farmed fish for human consumption, therefore, demands paying close attention to a combination of factors to minimize stress to the fish. The proper environmental conditions of temperature and pH, balanced nutrient delivery and regular provision of food, lack of overcrowding and minimal physical handling contribute to the overall health of fish stock. An imbalance or perturbation of one or more of these factors can significantly increase susceptibility to microbial infection and disease.

Fish microbial infection can be caused by primary or obligate pathogens that are not part of a normal aquatic flora, or by opportunistic pathogens that typically inhabit the water in which fish live. Infectious fish pathogens can establish themselves after any combination of stress to the fish. Physical trauma to the surface or skin of a fish can allow an opportunistic pathogen to penetrate the overlying mucoid and epidermal layers of the skin to reach the underlying tissues. The fish immune system can be compromised by adverse changes in the environmental conditions, such as unacceptable food or excessive handling. Should the water in which the fish are living become heavily contaminated with bacteria, the fish's own defenses against microbial invasion can be overwhelmed and an infection ensue.

Bacterial and fungal, and to a lesser extent protozoal, diseases are a frequent occurrence in the keeping of ornamental fish. If optimal conditions are not carefully maintained, or an infected fish is brought into the colony, an infectious microorganism can be introduced that will devastate a population of fish. Ornamental fish are susceptible to many of the same bacteria that cause disease in mammals and reptiles. Multiple species from, for example, the bacterial genera Aeromonas, Proteus, Streptococcus, Pseudomonas and Edwardsiella, have been implicated in morbidity and mortality of ornamental fish.

Three methods of treating a microbial infection of fish are typically used. Direct injection of antibiotics into the muscle or blood stream offers a high success rate against systemic infections, but is traumatic for the fish because of the necessary physical handling. Sedation can sometimes help to calm the animal. This procedure, however, is labor intensive and time-consuming, and is only a viable option for the treatment of small quantities of ornamental fish or the breeding stock used in fish-farming. Even then, injection is better reserved for the larger fish species and breeds such as koi, and goldfish, and farmed species such as catfish, salmon, and trout.

The second available treatment is to add antibiotics to fish feed. For the amateur breeder or keeper of ornamental fish, medicated fish foods are available from a veterinarian, but there may be an unacceptable delay in obtaining the medication before a fish succumbs to the infection. There is also evidence of over-use of antibiotics by ornamental fish breeders causing an increase in antibiotic resistance in bacteria. For the fish farmer, medicated foods can raise environmental concerns because of the discharge of untreated farm waste containing antibiotics not consumed by the fish, or which have survived excretion from the fish. The possibility of antibiotic release to the open environment and the potential to select for multiple or specific drug resistant mutants of bacteria requires strict regulation of the use of medicated foods in fish farming. Nitrifying bacteria useful in regulating the ammonia content of a tank can be reduced in number if antibiotics are added in high concentration in a culture tank. Also, the effectiveness of an antibiotic directly added to a fish tank may be limited by divalent ions such as calcium or magnesium that can bind and neutralize some antibiotics, especially tetracyclines and quinolones. Released antibiotics can also alter the ecological distribution of the microbial flora in the vicinity of the water release. A further problem with medicated foods is that sick fish may not ingest the food in the necessary therapeutic amounts or even at all. Even when successfully ingested, this treatment is best reserved for the treatment of internal systemic infections.

Bath treatments, or dips are a practical and simple means of treating surface infections of fish and lesions, such as skin ulcers. Although used to administer anesthetics to fish, or to apply pesticides to treat parasitic arthropod infestations such as sea lice infections of salmon, little use has been made of baths for administering antibiotics directed against microbial infections. Short-term treatment of surface bacterial infections such as fin rot, bacterial gill disease, or columnaris, a disease of the outer skin layer, can be achieved by bathing a fish in a weak potassium permanganate solution. Antibiotic baths, however, are seldom used to treat microbial infections in fish, and then only for surface or superficial infections. Deep ulcers and systemic diseases are typically treated with antibiotics administered by injection, food medication, or by merely isolating an infected fish to prevent the spread of the disease to the remainder of a population.

Unlike lavages that treat only the immediate area of infection, bath or dip treatments immerse the whole animal.

The fish may be left in the dip to ensure adequate exposure to the therapeutic agents. However, the bath ideally should be separate from a tank used to rear fish to prevent unnecessary exposure of fish stock to antibiotics. A separate tank also resolves environmental issues about disposal of large volumes of antibiotics from waste tank water.

In addition to fish, aquatic animals kept in tanks are also susceptible to surface bacterial infections. Animals captured or rescued from the wild may have infectious lesions that would benefit from an enhanced antibiotic activity and a simple means to administer an effective but safe therapeutic dose to the external surface of the animal. The limitations inherent in treatment methods of fish, however, apply equally to other aquatic species. Since the aqueous environment prevents the localized topical application of antibiotics unless the animal can be kept dry for a prolonged period on dry land, immersion baths are an important option in the treatment of infections on aqueous animals.

Regardless of the mode of administering an antibiotic solution to an animal, there is a constant possibility of inducing or selecting for antibiotic or multiple drug resistance by the bacteria. The wide-spread over-use of antibiotics in the fish-rearing industry has selected for highly resistant strains of bacteria that no longer respond to conventional antibiotic therapy. Although there is a paucity of data concerning antibiotic resistance in marine organisms, the increasing occurrence of microbial resistance to antibiotics might be expected. Any procedure that would enhance or otherwise supplement the potency of antimicrobial agents, therefore, would be invaluable for the effective treatment of microbial diseases.

The synergistic effects of combining an antibiotic with a chelating agent for the inhibition of bacterial growth have been reported in Wooley et al. *Am. J. Vet. Res.*, 36, 15331535 (1975); Bjorling & Wooley, *J. Am. Vet. Ed. Assoc.* 181, 596–597 (1982); Wooley et al., *Am. Vet. Res.* 43, 130–133 (1982); Wooley, R. E. *Mod. Vet. Pract.* 113–116 (February 1983); Wooley et al., *Am. Vet. Res.* 44, 2167–2169 (1983); Wooley et al., *Am. Vet. Res.* 44, 1521–1524 (1983); Wooley et al., *Vet. Microbiol.* 10, 57–70 (1984); Wooley & Jones, *Vet. Microbiol.* 8, 271–280 (1983); Wooley et al., *Vet. Microbiol.* 12, 65–75 (1986); Wooley et al.,*Am. Vet. Res.* 44, 1154–1158 (1983); Wooley et al., *Am. Vet. Res.* 42, 2010–2013 (1981); Wooley et al. *J. Am. Vet. Med. Assoc.* 175, 81–818 (1975); Sparks et al, *Vet. Res. Comm.* 18, 241–249 (1994). Similar compositions have also been disclosed for the flushing and coating of medical devices in U.S. Pat. No. 5,688,516 to Raad et al. incorporated herein by reference in its entirety.

SUMMARY OF THE INVENTION

There is a need for methods of treating microbial infections of animals, especially aquatic animals, more especially fish, that allow for reduced doses of antibiotics while maintaining antibiotic efficacy. Antibiotic baths are also required in which fish may be immersed for effective treatment of a microbial infection without toxic or harmful effects to the fish. The methods of treatment of microbial fish infections of the present invention can be adapted for a number of antibiotics biologically active against bacteria and acceptable for use in fish intended for human consumption.

The methods of the present invention are particularly useful for enhancing the potency of an antibiotic when acting against a microbial organism having resistance to the antibiotic.

The present invention, therefore, provides methods of using aqueous antibiotic baths or dips that incorporate compounds to enhance the activity of antibiotics and allow lower effective concentrations of the antibiotic.

The present invention provides novel methods of reducing bacterial infections of aquatic animals, especially of fish maintained in tanks, aquaria, or ponds. The aqueous environment of fish, even when in tanks, would otherwise require large quantities of antibiotics to ensure the fish are bathed in adequate antibiotic concentrations that are effective against the infection, while not toxic to the fish themselves.

The present invention provides methods for reducing a microbial infection of an aquatic animal, comprising the steps of dissolving an antimicrobial composition in a carrier to give an antimicrobial solution, wherein the antimicrobial composition comprises at least one chelating agent and at least one antibiotic, immersing an aquatic animal in the antimicrobial solution, removing an aquatic animal from the antimicrobial solution, and placing an aquatic animal in water not containing the antimicrobial composition.

One embodiment of the present invention, for example, provides a method for reducing a microbial infection of an aquatic animal, comprising the steps of selecting an aquatic animal having a microbial infection, providing an antimicrobial solution comprising the chelating agents EDTA or TRIENE, and at least one antibiotic, adding a pH buffering agent to the antimicrobial solution and adjusting the pH thereof to a value of between about 7.0 and about 9.0, immersing the aquatic animal in the antimicrobial solution and leaving the aquatic animal therein for a period that is effective to reduce the microbial burden of the animal, removing the aquatic animal from the antimicrobial solution and returning the animal to water not containing the antimicrobial solution. The immersion of the aquatic animal in the antimicrobial solution containing the EDTA, antibiotic, or TRIENE and pH buffering agent may be repeated until the microbial burden of the animal is eliminated.

The present invention further provides kits for use in reducing a microbial infection of a marine or freshwater aquatic animal, comprising at least one container having therein at least one chelating agent, and optionally at least one antibiotic, and packaging material, wherein the packaging material comprises instructions directing the use of the kit for administering the antibiotic and chelating agent to inhibit the proliferation of a microbial infection of an aquatic animal.

Additional objects, features, and advantages of the invention will become more apparent upon review of the detailed description set forth below when taken in conjunction with the accompanying drawing figures, which are briefly described as follows.

DETAILED DESCRIPTION OF THE INVENTION

Figure 1:
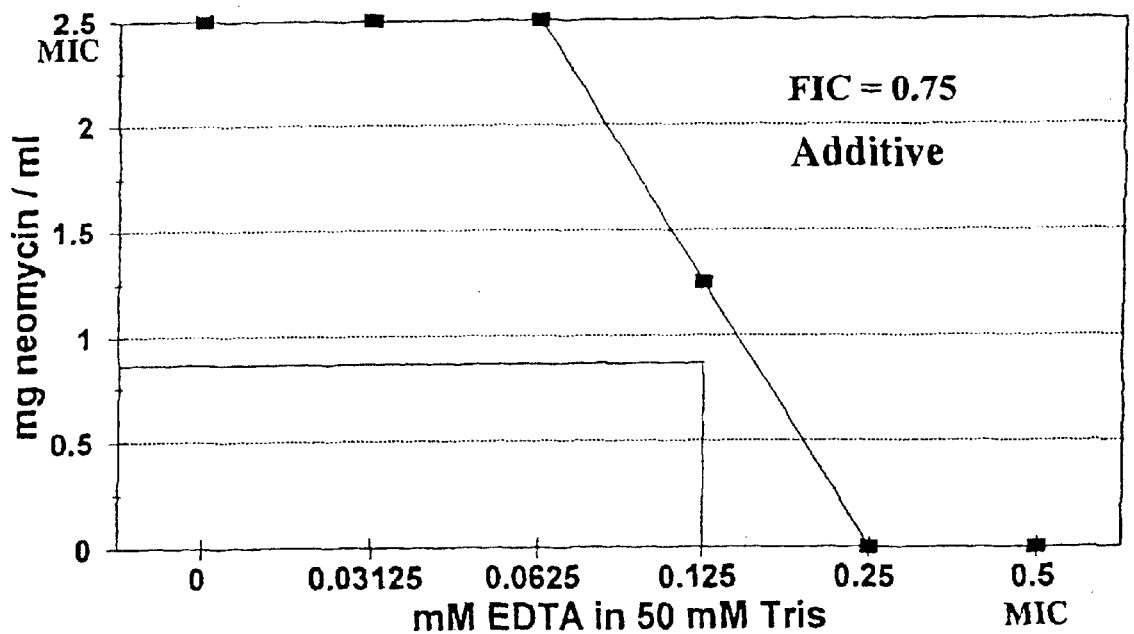
FIG. 1. Isobologram, illustrating the combined effect on *Staphylococcus aureus* growth of EDTA and neomycin in 50 mM Tris buffer.

A full and enabling disclosure of the present invention, including the best mode known to the inventor of carrying out the invention is set forth more particularly in the remainder of the specification, including reference to the Examples. This description is made for the purpose of illustrating the general principles of the invention and should not be taken in the limiting sense.

The present invention provides methods for inhibiting the growth of microbial infections of aquatic animals, especially of fish maintained in tanks, aquaria, or ponds. The methods of the present invention combine at least one metal chelating agent and at least one antibiotic that is biologically active against bacterial infections and, optionally, at least one pH buffering agent, wherein the antimicrobial activity of the antibiotic is enhanced by the chelating agent. The method of the present invention is effective against microbial infections that heretofore have resisted treatment by antibiotics alone. The aqueous environment of fish requires large amounts of antibiotics be used to bathe a fish in solutions effective against the bacteria, while not toxic to the fish themselves. The methods of the present invention are useful for enhancing the antimicrobial activity of an antibiotic, thereby reducing the amount of the antibiotic necessary in a water bath, while still maintaining a therapeutic level of antimicrobial activity.

The present invention combines at least one antibiotic with a chelating agent. Exemplary chelating agents include, but are not limited to, EDTA or TRIENE. While not wishing or intending to be bound by any particular theory, it is believed that a suitable chelating agent has a three-fold function. First, it reduces the level of divalent metal ions in the water that could otherwise combine with, and effectively neutralize, some antibiotics. Secondly, the chelating agent removes divalent metal ions from the cell walls of microorganisms, and in particular of bacteria, and so weakening the integrity of the wall. This allows antibiotics to more readily penetrate the wall. Thirdly, the chelator may create pores in the microbial cell wall that facilitate entry of antibiotics into the microbial cell and leakage of the cellular contents therefrom, and reduces the viability of the microorganism.

The present invention further optionally provides a pH buffering agent such as, but not limited to, Tris base that can maintain an optimum pH for the selected antibiotic activity.

The present invention also provides kits that include at least one chelating agent, at least one antibiotic, at least one pH buffering agent and packaging that comprises instructions for the preparation of a solution of the antimicrobial compositions and their use in treating an aquatic animal having a microbial infection.

Definitions

The term "microbial infection" as used herein refers to any pathological or non-pathological presence of at least one bacterial species on or in an aquatic animal, and which may be treated by an antibiotic-containing bath or dip of the animal.

The term "inhibiting the proliferation of a microbial population" as used herein refers to the bacteristatic or bacteriocidal activity of an antimicrobial composition. A bacteristatic antimicrobial composition will inhibit the multiplication of a bacterial population. A bacteriocidal antimicrobial composition will contact and kill the target microbial population.

The terms "marine" or "freshwater" as used herein refer to the natural environment of an aquatic animal. The term "marine" refers to any environment relating to the oceans or seas wherein the water is saline. The term "freshwater" refers to, but is not limited to, lakes, ponds, rivers, streams, brooks or any other low salinity water.

The term "aquatic animal" as used herein refers to any animal that spends all or some of its life in marine or fresh water. An "aquatic animal" can be, but is not limited to, a mammal such as a seal, sea lion, walrus, manatee, dugong, porpoise, dolphin, cetaceous or non-cetaceous whale, otter, or beaver; a bird such as, but not limited to, a web-footed bird such as a duck, goose, swan, gull, cormorant, penguin, a wading bird such as a coot, moor hen, flamingo, stork, heron; an aquatic reptile such as, but not limited to, an alligator, cayman, crocodile, turtle, snake or lizard; an amphibian such as, but not limited to, frogs, toads, newts and salamanders, neotenous larva or larvae thereof; fish and aquatic invertebrates such as, but not limited to, crustacea, insects, or molluscs.

The term "fish" as used herein refers to any marine or freshwater fish species maintained in a tank, aquarium, pool, pond, aquaculture facility, fish farm, or any means other than the natural environment of the fish species. The term "fish" also refers to species and individuals thereof captured, rescued or taken from their native habitat and which may require treatment for microbial infestations. Fish species to which the methods of the present invention may be applied include, but are not limited to, ornamental fish, goldfish, koi, oscar, cichlids, tropical fish and fish for human or animal food such as, but not limited to, catfish, and salmonids such as trout, or salmon.

The term "chelating agent" as used herein refers to any organic or inorganic compound that will bind to a metal ion having a valence greater than one. "Chelating agents" include, but are not limited to, organic chelating agents such as ethylenediamenetetracetic acid (EDTA), triethylene tetramine dihydrochloride (TRIEN), ethylene glycol-bis (β-aminoethyl ether-N, N, N', N'-tetracetic acid (EGTA), diethylenetriamin-pentaacetic acid (DPTA), and triethylenetetramine hexaacetic acid (TTG), deferoxamine, Dimercaprol, edetate calcium disodium, zinc citrate, penicillamine succimer and Editronate or any other chelating agent that will chelate divalent ions such as $Ca^{2+}$, $Mg^{2+}$, $Mn^{2+}$, $Fe^{2+}$, and $Zn^{2+}$, and which are biologically acceptable to aquatic animals.

The term "antibiotic" as used herein refers to any compound known to one of ordinary skill in the art that will inhibit the growth of, or kill, bacteria. The term "antibiotic" includes, but is not limited to, β-lactams (penicillins and cephalosporins), vancomycins, bacitracins, macrolides (erythromycins), lincosamides (clindomycin), chloramphenicols, tetracyclines, aminoglycosides (gentamicins), amphotericins, cefazolins, clindamycins, mupirocins, sulfonamides and trimethoprim, rifampicins, metronidazoles, quinolones, novobiocins, polymixins, gramicidins or any salts or variants thereof It is understood that it is within the scope of the present invention that the tetracyclines include, but are not limited to, immunocycline, chlortetracycline, oxytetracycline, demeclocycline, methacycline, deoxycycline and minocycline.

The term "carrier" as used herein refers to any pharmaceutically acceptable solvent of antibiotics, chelating agents and pH buffering agents that will allow the antimicrobial composition of the present invention to be administered directly to an aquatic animal. A "carrier" as used herein, therefore, refers to such solvent as, but is not limited to, water, saline, physiological saline, ointments, creams, oil-water emulsions or any other solvent or combination of solvents and compounds known to one of skill in the art that is pharmaceutically and physiologically acceptable to the recipient animal. The term "carrier" further includes vitamin E or the like that may comprise an oily film over the site of application on the surface of an animal.

The term "pH buffering agent" as used herein refers to any organic or inorganic compound or combination of compounds that will maintain the pH of an antimicrobial solution such as an antibiotic bath, to within about 0.5 pH units of a selected pH value. A "pH buffering agent" may be selected from, but is not limited to, Tris (hydroxymethyl) aminomethane (tromethaprim; TRIZMA base), or salts thereof, phosphates or any other buffering agent that is physiologically acceptable to an aquatic animal.

The term "disease" as used herein refers to a pathological condition recognizable as an abnormal condition of an animal. A "fish disease" is a pathological condition of fish that may be fatal or benign such as, but not limited to, ulcers, fin rot, dropsy, Malawi bloat disease, gill disease and columnaris or saddlepatch disease.

Microbial species that may cause infections inhibited by the methods of the present invention include bacteria such as, but not limited to, *Aerobacter aerogenes, Aeromonas hydrophila, Bacillus cereus, Bacillus subtilis, Bordetella pertussis, Borrelia burgdorferi, Campylobacter fetus, C. jejuni, Corynebacterium diphtheriae, C. bovis*, Cytophagia, *Desulfovibrio desulfurica*, Edwardsiella, *Escherichia coli*, enteropathogenic *E. coli*, Enterotoxin-producing *E coli*, Flavobacterium spp., Flexibacter, *Helicobacter pylori, Klebsiella pneumoniae, Legionella pneumophiia, Leptospira interrogans, Mycobacterium tuberculosis, M. bovis, N. meningitidis, Proteus mirabilis, P. vulgaris, Pseudomonas aeruginosa, Rhodococcus equi, Salmonella choleraesuis, S. enteridis, S. typhimurium, S. typhosa, Shigella sonnet, S. dysenterae, Staphylococcus aureus, Staph. epidermidis, Streptococcus anginosus, S. mutans, Vibrio cholerae, Yersinia pestis, Y. pseudotuberculosis*, Actinomycetes spp., *Streptomyces reubrireticuli, Streptoverticillium reticulum*, and *Thermoactinomyces vulgaris*.

The term "biologically active" as used herein refers to the ability of an antibiotic to inhibit the proliferation of a microorganism. The action of the antibiotic can be either bacteriostatic, wherein the antibiotic arrests, but does not necessarily kill, the microorganism or bacteriocidal, wherein the action of the antibiotic kills the organism, or manifest a combination of bacteriostatic and bacteriocidal activity.

Techniques to identify the infecting microorganism and to determine the concentration of the antibiotic that will inhibit or kill fifty percent (Minimal Inhibitory Concentration—$MIC_{50}$) of the infecting organisms are well known to one of ordinary skill in the art and will not require undue or excessive experimentation.

A standard manual to determine the antibiotic sensitivity of a particular bacterial isolate is Manual of Methods for General Microbiology, Eds: Gerhardt et al., *American Society of Microbiology*, 1981, incorporated herein by reference in its entirety. Methods of determining the synergistic effect of adding a chelating agent to a solution of an antibiotic are described in Manual of Methods for General Microbiology, Eds: Gerhardt et al., *American Society of Microbiology*, 1981 and in Wooley et al. *Am. J. Vet. Res.*, 36, 1533–1535 (1975); Bjorling & Wooley, *J. Am. Vet. Ed. Assoc.* 181, 596–597 (1982); Wooley et al., *Am. Vet. Res.* 43, 130–133 (1982); Wooley, R. E. *Mod. Vet. Pract.* 113–116 (February 1983); Wooley et al., *Am. Vet. Res.* 44, 2167–2169 (1983); Wooley et al., *Am. Vet. Res.* 44, 1521–1524 (1983); Wooley et al., *Vet. Microbiol.* 10, 57–70 (1984); Wooley & Jones, *Vet. Microbiol.* 8, 271–280 (1983); Wooley et al., *Vet. Microbiol.* 12, 65–75 (1986); Wooley et al., *Am. Vet. Res.* 44, 1154–1158 (1983); Wooley et al., *Am. Vet. Res.* 42, 2010–2013 (1981); Wooley et al. *J. Am. Vet. Med. Assoc.* 175, 81–818 (1975); and Sparks et al, *Vet. Res. Comm.* 18, 241–249 (1994), all incorporated herein by reference in their entireties.

The present invention provides methods for bathing, flushing or dipping an aquatic animal in a bath or tank containing an antimicrobial solution, and kits containing the agents that together comprise an antimicrobial solution for the treatment of a microbial infection. The kits further include instructions that will direct the user of the kit to prepare an antimicrobial bath according to the present invention. While the method of administration of the solution of the present invention is especially suited for application to aquatic animals that may withstand a prolonged immersion, any animal may be dipped or immersed in the antimicrobial solution. Immersion or dipping of the animal in the antimicrobial solution may be a single event or repeated events, the total accumulation of time in the solution depending upon the degree of clearance of the infection from the animal. A useful period for a fish to be immersed in the antimicrobial solutions of the present invention is about 5 minutes, which minimizes exposure of the animal to the solutions while providing an effective exposure to inhibit microbial proliferation thereon. The optimum time for immersion of a fish depends upon the species treated, and the sensitivity to the antimicrobial composition of the present invention. For example, koi may prefer a 5 minute immersion period, whereas catfish may tolerate between about 10–15 minutes without manifesting adverse reactions. It is further contemplated by the present invention that the antimicrobial solution may be a shallow bath that could be used to treat an infection of an isolated body part, such as a foot of an animal. The site of the infection is exposed to the antibiotic solution by the animal walking through the shallow bath or by dipping only that body part in the bath.

In one embodiment of the method of the present invention the animal to be treated with the antimicrobial solution is an aquatic animal that can survive a period of immersion in an aqueous solution such as the antimicrobial solution of the present invention. In another embodiment of the present invention, the aquatic animal to be treated is an ornamental fish or a fish raised by aquaculture for consumption, such as, but not only, catfish, salmon, or trout. The present invention further contemplates, however, that any animal can be dipped in a bath of an antimicrobial solution for treatment of a skin infection.

The method of the present invention comprises selecting an animal having a microbial infection requiring treatment. The infection may be any bacterial disease of the exterior surface of the animal, such as, but not limited to, an ulcer or any other surface lesion or disease of fish recognized by one of ordinary skill in the art.

The antimicrobial solution of the present invention comprises an antibiotic effective against the microbial organism causing a disease on an animal, and a chelating agent. It is within the scope of the present invention that the antibiotic is biologically active against a bacterium capable of establishing an infectious disease of an animal, and especially of the external surface of an animal. The method may also comprise the steps of identifying the species of bacteria that colonize or infect and determining the antibiotic sensitivity spectrum. The MIC and FIC of an effective antibiotic and a chelating agent may then be determined and an optimum dose of antibiotic in the presence of the chelating agent may be calculated, thereby minimizing exposure of the animal and bacteria to the antibiotic, thus reducing harmful effects to the aquatic animal, while maintaining efficacy against the bacteria.

In one embodiment of the present invention, the antibiotic may be one, or more than one, antibiotic effective against Gram-positive or Gram-negative bacteria. In another embodiment the antibiotic may be selected from a β-lactam, aminoglycoside, vancomycin, bacitracin, macrolide, erythromycin, lincosamide, chloramphenicol, tetracycline, gentamicin, amphotericin, cefazolin, clindamycin, mupirocin, nalidixic acid, sulfonamide and trimethoprim, streptomycin, rifampicin, metronidazole, quinolone, novobiocin, polymixin or gramicidin, or any salt thereof In one embodiment the antibiotic may be selected from a penicillin, aminoglycoside, vancomycin, chloramphenicol, erythromycin, tetracycline, gentamicin, nalidixic acid, and a streptomycin. In yet another embodiment the antibiotic is oxytetracycline. In another embodiment of the present invention the antibiotic is gentamicin. In yet another embodiment of the present invention the antibiotic is amikacin. In still another embodiment of the present invention, the antibiotic is neomycin. The concentration of the antibiotic will not be toxic to the animal itself. In one embodiment, the concentration of the antibiotic is in the range of about 0.005 mg/ml to about 25.0 mg/ml. In another embodiment, the range of the concentration of the antibiotic is between about 0.05 to about 2.0 mg/ml. In yet another embodiment, the range of the concentration antibiotic is between about 0.005 mg/ml and 2.0 mg/ml.

The antimicrobial solution of the present invention further comprises a chelating agent that enhances the antimicrobial activity of the antibiotic. Any chelating agent known to one of ordinary skill in the art and which is physiologically acceptable to the treated animal may be used in the present invention to chelate multivalent metal ions such as, but not limited to, calcium, magnesium, manganese, iron, copper, cobalt and the like that might interact with, and reduce the efficacy of, an antibiotic. Alternatively, the chelating agent can remove a divalent metal ion from a target microbial cell. While not wishing to be bound by any one theory, the removal of divalent metal ions from the structure of the bacterial cell wall can weaken the integrity of the wall so that it is more susceptible to disruption by the antibiotic. The chelating agent may also create pores in the cell wall that may facilitate entry of the antibiotic into the wall or the cell proper, and increasing the effective activity of the antibiotic against the microbe. The selected chelating agent is preferably non-toxic and physiologically acceptable to the animal being treated or, if toxic, is administered at a concentration that will not harm the animal. The application of a composition comprising an antibiotic and a chelating agent, as in the present invention, may also include enhanced healing action wherein stimulation of at least one component of a fish immune system will lead to a reduction in the microbial burden of a fish, and also promote cell growth and healing of the lesion of the fish.

In one embodiment of the present invention the chelating agent is selected from ethylenediamenetetracetic acid (EDTA), triethylene tetramine dihydrochloride (TRIEN), ethylene glycol-bis (β-aminoethyl ether)-N, N, N', N'-tetracetic acid (EGTA), diethylenetriamin-pentaacetic acid (DPTA), triethylenetetramine hexaacetic acid (TTG), deferoxamine, Dimercaprol, edetate calcium disodium, zinc citrate, penicilamine succimer and Editronate.

In another embodiment of the present invention, the chelating agent is selected from ethylenediamenetetracetic acid (EDTA), triethylene tetramine dihydrochloride (TRIEN), ethylene glycol-bis (β-aminoethyl ether)-N, N, N', N'-tetracetic acid (EGTA), diethylenetriamin-pentaacetic acid (DPTA), and triethylenetetramine hexaacetic acid (TTG). In another embodiment, the chelating agent is ethylenediamenetetracetic acid (EDTA) or triethylene tetramine dihydrochloride (TRIEN).

In one embodiment of the present invention the chelating agent has a concentration in the solution of between about 0.1 mM and about 50 mM. In another embodiment, the concentration of the chelating agent is between about 0.1 mM and about 10 mM.

Since an antibiotic and a chelating agent may interact more effectively at one specified pH than at another, the present invention contemplates that the antimicrobial solution further comprises an optional pH buffering agent that is physiologically acceptable to an animal treated with the antimicrobial solution. In one embodiment, the pH buffering agent is Tris (hydroxymethyl) aminomethane (TRIZMA Base), has a concentration in the antimicrobial solution of between about 10 mM and about 100 mM, and maintains the pH in the range of about 7.0 to about 9.0. While one of ordinary skill in the art will recognize that any physiologically acceptable concentration and pH value is within the scope of the present invention, in another embodiment the buffering agent is 50 mM Tris and maintains the pH value at about 8.0.

Even though the invention has been described with a certain degree of particularity, it is evident that many alternatives, modifications, and variations will be apparent to those skilled in the art in light of the present disclosure. Accordingly, it is intended that all such alternatives, modifications, and variations that fall within the spirit and the scope of the invention be embraced by the defined claims.

The following examples are presented to describe preferred embodiments and utilities of the present invention, but should not be construed as limiting thereof.

It should be appreciated by those of skill in the art that the techniques disclosed in the examples which follow represent techniques discovered by the inventors to function well in the practice of the invention, and thus can be considered to constitute preferred modes for its practice. Those of skill in the art should, however, in light of the present disclosure, appreciate that many changes can be made in the specific embodiments disclosed and still obtain like or similar results without departing, again, from the spirit and scope of the present invention.

EXAMPLE 1

Non-toxicity of Tris-EDTA to Fish

An in vivo evaluation of Tris-EDTA was conducted on SPF (specific pathogen free) catfish. After a 15 minute immersion time, the catfish showed no ill effects. With a 30 minute incubation period, however, the fish rolled but recovered when removed from the dip. None of the fish exhibited any long-term side effects from the immersion treatment with Tris-EDTA.

EXAMPLE 2

An Antibiotic-EDTA Composition is Effective in Treating a Microbial Infection of Fish The data show that a bath treatment with EDTA-Tris in conjunction with a number of antibiotics was well tolerated by fish and was effective in healing ulcerated lesions that had not responded to traditional antibiotic therapy, such as an injection of antibiotics or medicated food. An immersion treatment of the infected animals of 5 to 10 minutes on alternate days over a six day period promoted healing of most ulcers.

Ten Koi (*Cyprinus carpio*) obtained from a commercial fish hatchery and suffering from surface ulcers, were treated by immersion in 50 mM Tris (Tris-[hydroxy-methyl]-aminomethane) and 5 mM EDTA (ethylenediaminetetracetic acid) containing the antibiotic neomycin (140 mg/100 ml) for 10 minutes.

All of the treated fish had previously been given injections of Azactam, Baytril, and amikacin. These antibiotics, when injected directly into the fish, had failed to heal visible ulcers. Culture and sensitivity testing of the microbial population present in the ulcers revealed multiple pathogenic species that were highly resistant to conventional antibiotic treatment. Among the species of bacteria found in the ulcers of the fish were representatives of the genera Aeromonas, Proteus, Klebsiella, Staphylococcus, Streptococcus, Enterobacter and Flavobacterium.

All fish were housed in a communal "hospital tank" before treatment and moved to an isolation tank after each treatment. The temperature of the bath was adjusted to that of the hospital tank temperature, 24° C., and adequate aeration was supplied to the treatment tank. Eight of the fish had external ulcers of various dimensions. Two of the fish were dropsied.

Fish displayed no signs of stress other than becoming hyperemic, which is typical for Koi when handled. Ulcers appeared less red after the first dip treatment and were significantly diminished after two subsequent dips. One of the dropsied fish died, and a Tancho with an ulcer died two days after therapy was begun. Both of these fish, however, had systemic bacterial infections in addition to external lesions.

EXAMPLE 3

Determination of Effectiveness of Antibiotic-EDTA Treatment of Ulcerated Fish Compared to No Treatment A group of 20 ulcerated Koi, each 7.5 cm–10 cm long, were treated with the Tris/EDTA and neomycin immersion treatment together with an untreated control group of fish with similar lesions from the same source. Two of the treated fish with sizable lesions died during treatment. All fish were placed in flow-through 20 gallon aquariums and observed daily. A total of three treatments were administered on alternate days.

Lesions began to heal in the treated group, while the fish steadily declined in health in the untreated control group. As the lesions worsened in the untreated control group, mortalities occurred. The 18 fish in the treatment group, however, responded to therapy and the ulcerated lesions healed.

EXAMPLE 4

Determination of Synergistic Actions and the Fractional Inhibitory Concentration of an Antimicrobial Agent-Chelator Composition (FIC) Index The antibacterial action of combinations of EDTA-Tris and neomycin was measured by a two-dimensional microtiter checkerboard technique described in Gilman et al., *The Pharmacological Basis of Therapeutics*, eds Goodman and Gilman, 1085–1086 (Macmillan Publishing Co., New York, 1985),. Sabath, L. D, *Antimicrob. Agents and Chem.* 210–217. (1967) and Sparks et al., *Vet. Res. Comm.* 18, 241–249 (1994), incorporated herein by reference in their entireties.

Each well of a round-bottomed 96-well microtiter plate was inoculated with 0.05 ml of 2-fold dilutions of neomycin, and of EDTA in 50 mM Tris. Then 0.05 ml of an 18-hour old culture of a test organism, containing $10^6$ colony-forming units (CFU) ml, were added to each well. Controls for the culture and media were included in each plate. Plates were covered and incubated at 37° C. for 18–24 hours.

Results were plotted as isobolograms for the determination of antagonistic, neutral or additive, or synergistic effects. To generate isobolograms, FICs of the two test solutions were plotted individually on the x-axis and y-axis to determine the effect of combining the two test solutions on bacterial growth. A line that curves away from the zero point and the coordinates indicated antagonism. A straight line indicated neutral or additive effects. Lines that curved toward the zero point and the coordinates indicated synergism if there was at least a 4-fold decrease in the MIC of each compound, when used in combination, as compared with the MIC of each test compound alone as described in Gilman et al., *The Pharmacological Basis of Therapeutics*, eds Goodman and Gilman, 1085–1086 (Macmillan Publishing Co., New York, 1985),. Sabath, L. D, *Antimicrob. Agents and Chem.* 210–217. (1967), and incorporated herein by reference in their entireties.

A numerical score or Fractional Inhibitory Concentration (FIC) index was determined. The FIC index is equal to the sum of the values of FIC for the individual drugs:

$$FIC = \frac{\text{MIC of Drug A with Drug B}}{\text{MIC of Drug A}} + \frac{\text{MIC of Drug B with Drug A}}{\text{MIC of Drug B}}$$

An FIC index greater than 1.0 indicated an antagonistic interaction, an FIC index of 1.0 indicated addition, and an FIC index of less than or equal to 0.5 indicated synergism between the two test agents.

EXAMPLE 5

In Vitro Effect of EDTA-Tris and Neomycin on *Enterococcus faecalis, Pseudomonas aerueinosa*, and *Staphylococcus aureus* Growth 2×NA plates were swabbed with 200 ml of an overnight bacterial culture containing about $10^7$ colony-forming-units of a test organism. The plates were sampled with multipoint contactors as described in Wooley et al., *Am. J. Vet. Res.* 35, 807–810. (1974), incorporated herein by reference in its entirety. Each multipoint contactor consisted of an array of 100 of 27 mm sewing needles mounted to an aluminum plate measuring 1 mm×50 mm×50 mm. The needles were set 3.5 mm apart. The multipoint contactors were sterilized by autoclaving. To collect samples, a multipoint contactor was touched to an overnight bacterial culture grown on 2×NA as described above. Replicate plates were then inoculated by lightly pressing the needles bearing the test bacteria onto either MHA plates, BA plates or EA plates for *Ps. aeruginosa, Staph. aureus* and *Ent. faecalis* respectively. The agar plates were incubated at 37° C. and colonies were counted at 24 hours and 48 hours.

Each strain of microorganism was tested on a control agar plate (plate 1), and on plates wherein the inoculated bacteria were covered with a sterile surgical gauze saturated with 7 ml of: 5 mM EDTA, 50 mM Tris (plate 2); 5 mM EDTA, 50 mM Tris and 1 mg/ml neomycin (plate 3); 1 mg/ml neomycin (plate 4); sterile water (plate 5). Samples were taken at 0 mins, and at 30 mins, 1 hour, 2 hours, 4 hours, 6 hours, 8 hours, and 24 hours of incubation.

EXAMPLE 6

The Antibiotic Resistance Profiles, MIC and MBC Values for Test Strains of *Staph. aureus, Ps. aeruginosa*, and *Ent. faecalis*

The antibiotic resistance profiles and MIC values for test strains of *Staph. aureus, Ps. aeruginosa*, and *Ent. faecalis* are shown on Table 1.

TABLE 1

Antibiotic resistance profiles of *Staphylococcus aureus, Pseudomonas aeruginosa*, and *Enterococcus faecalis*.

| | Antimicrobial Agents[A] | | | | | | | | | | |
|---|---|---|---|---|---|---|---|---|---|---|---|
| | Am | C | Cip | Gm | K | NA | N | S | G | Te | Va |
| *Staphylococcus aureus* | R[B] | I | R | S | R | R | R | S | S | S | S |
| *Pseudomonas aeruginosa* | R | R | I | I | R | R | R | R | R | R | R |
| *Enterococcus faecalis* | S | R | R | R | R | R | R | R | R | R | R |

[A]Am = ampicillin; C = chloramphenicol; Cip = ciprofloxacin; K = kanamycin; Gm = gentamicin; NA = nalidixic acid; N = neomycin; S = streptomycin; G = sulfisoxazole; Te = tetracycline; Va = vancomycin;
[B]R = resistant; I = intermediate; S = sensitive.

Figure 2:
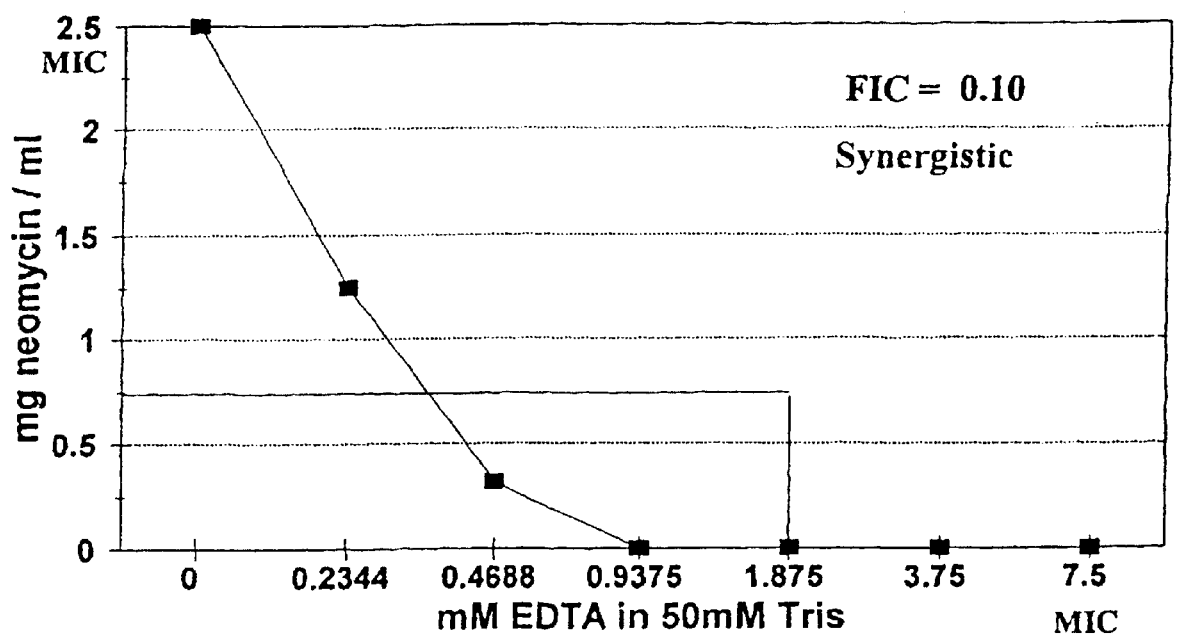
FIG. 2. Isobologram, illustrating the combined effect on *Pseudomonas aeruginosa* growth of EDTA and neomycin in 50 mM Tris buffer.
Figure 3:
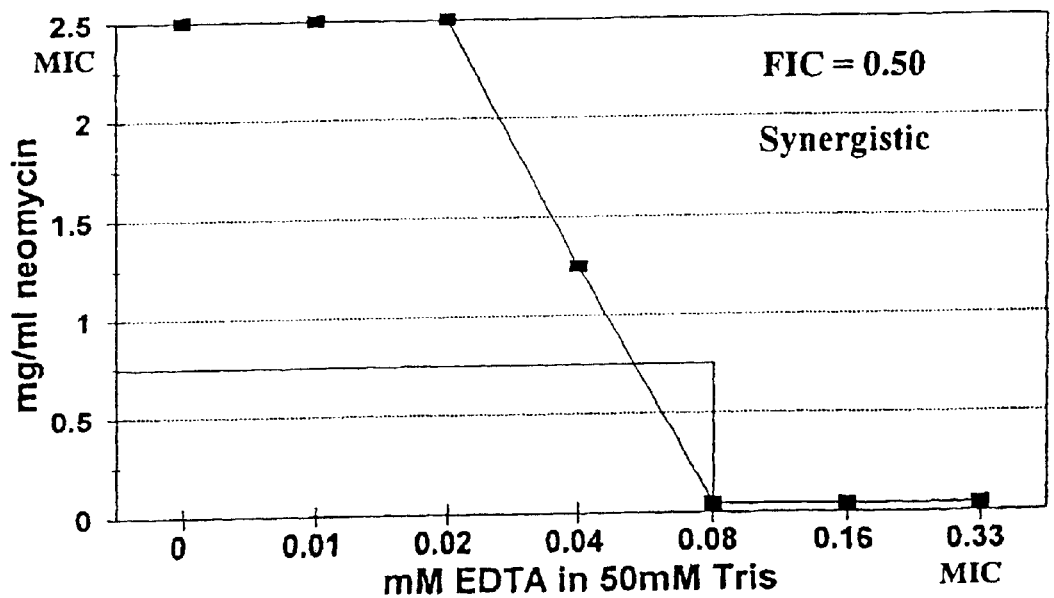
FIG. 3. Isobologram, illustrating the combined effect on *Enterococcus faecalis* growth of EDTA and neomycin in 50 mM Tris buffer.

Fractional inhibitory concentrations (FICs) and isobolograms for the EDTA-Tris, neomycin combination to determine a synergistic, additive, or antagonistic reaction, as described in Example 1, were determined for *Staph. aureus, Ps. aeruginosa*, and *Ent. faecalis* as shown in FIGS. 1–3. MIC and MBC values for concentrations of neomycin, ampicillin, chloramphenicol, amikacin and oxytetracycline and EDTA administered individually, and the FIC values for *Staph. aureus, Ps. aeruginosa*, and *Ent. faecalis* are shown in Table 2 (Columns 2 and 3). MIC values for mixtures of the above antibiotics and EDTA in the presence of each other are shown in Table 2 (Columns 4 and 5 respectively).

TABLE 2

Minimal Inhibitory Concentration (MIC) data concerning the amounts (mM) of EDTA in 50 mM Tris and antibiotics (mg/ml) when reacting alone and in combination against *Ps. aeruginosa, Staph. aureus*, and *Ent. faecalis*.

| | MIC | | | | |
|---|---|---|---|---|---|
| | Individually Administered | Individually Administered EDTA | Co-administered | | FIC |
| | Neomycin | | Neomycin + EDTA | | |
| *Ps. aeruginosa* | 1.0 | 1.25 | 0.063 | 0.156 | 0.19 |
| *Staph. aureus* | 3.13 | 1.0 | 1.56 | 0.25 | 0.75 |
| *Ent. faecalis* | 3.13 | 15.63 | 1.17 | 1.88 | 0.5 |
| | Ampicillin | | Ampicillin + EDTA | | |
| *Ps. aeruginosa* | 0.49 | 1.25 | 0.123 | 0.156 | 0.38 |
| *Staph. aureus* | 0.24 | 1.0 | 0.0075 | 0.25 | 0.28 |
| *Ent. faecalis* | 0.001 | 15.63 | 0.00025 | 7.82 | 0.75 |
| | Chloramphenicol | | Chloramphenicol + EDTA | | |
| *Ps. aeruginosa* | 12.5 | 1.25 | 1.56 | 0.313 | 0.37 |
| *Staph. aureus* | 0.39 | 1.0 | 0.39 | 1.0 | 2.0 |
| *Ent. faecalis* | 0.4 | 15.63 | 0.2 | 3.9 | 0.75 |
| | Amikacin | | Amikacin + EDTA | | |
| *Ps. aeruginosa* | 0.001 | 1.25 | 0.001 | 1.25 | 2.0 |
| *Staph. aureus* | 0.12 | 1.0 | 0.03 | 0.5 | 0.75 |
| *Ent. faecalis* | 2.0 | 15.63 | 1.0 | 7.8 | 1.0 |
| | Oxytetracycline | | Oxytetracycline + EDTA | | |
| *Ps. aeruginosa* | 0.003 | 1.25 | 0.00075 | 0.313 | 0.5 |
| *Staph. aureus* | 0.0001 | 1.0 | 0.00005 | 0.5 | 1.0 |
| *Ent. faecalis* | 0.05 | 15.63 | 0.025 | 3.91 | 0.75 |

*Synergistic reaction (FIC = ≦0.5)
Additive reaction (FIC = >.05 to ≦1.0)
Antagonistic reaction (FIC = >1.0)

The MBC values for EDTA and neomycin were decreased by at least 75% for bacterial killing (MCB) in those situations in which synergistic potentation occured (*Ps. aeruginosa* and *Ent. faecalis*) as shown in Table 3. A decrease of about 50% was observed with *Staph. aureus*.

TABLE 3

Minimal Bactericidal Concentrations (MBC), of *Staph. aureus*, *Ps. aeruginosa*, and *Ent. faecalis* reacted with EDTA (mM) and neomycin (mg/ml) in 50 mM Tris.

| Bacterial Species | | Individually Administered | Co-administered |
|---|---|---|---|
| *Staphylococcus aureus* | EDTA (mM) | 7.81 | 3.9 |
| | Neomycin (mg/ml) | 3.13 | 1.56 |
| *Pseudomonas aeruginosa* | EDTA (mM) | 250 | 20.0 |
| | Neomycin (mg/ml) | 5.0 | 0.04 |
| *Enterococcus faecalis* | EDTA (mM) | 250 | 62.5 |
| | Neomycin (mg/ml) | 25.0 | 6.25 |

Specifically in the case of *Staph. aureus*, the MBC values for EDTA and neomycin when combined were decreased by 50% as compared to the bactericidal effect of each when individually administered.

With *Ps. aeruginosa*, the MBC values for EDTA and neomycin when in combination were decreased 99.2% compared to when EDTA or neomycin were individually administered. In the case of *Ent. faecalis*, MBC values of EDTA and neomycin were both reduced 75% compared to when EDTA and neomycin were administered individually.

Synergistic effects were observed when various concentrations of EDTA-Tris and neomycin were reacted with *Ps. aeruginosa* and *Ent. faecalis*, while an additive effect was observed with *Staph. aureus* as shown in FIGS. 1–3.

EXAMPLE 7

MIC and FIC Values for Test Species of *Aeromonas spp.* Isolated from Fish

The MICs for EDTA and neomycin were determined with three species of Aeromonas isolated from ulcerated fish, as shown in Table 4.

TABLE 4

Minimal Inhibitory Concentration (MIC) data for EDTA in 50 mM Tris and neomycin (mg/ml) when reacted alone or in combination against *Aeromonas hydrophila*, *Aeromonas sobria*, and *Aeromonas caviae*.

| Aeromonas sp. | Neomycin | EDTA | Neomycin + EDTA | | FIC |
|---|---|---|---|---|---|
| A. hydrophila | 0.2 | 250 | 0.1 | 62.5 | 0.7 |
| A. sobria | 0.0125 | 15.6 | 0.0075 | 3.88 | 0.31 |
| A. caviae | 0.0125 | <0.49 | 0.00625 | <0.25 | 1.0 |

EXAMPLE 8

Antibiotic Resistance Profiles

Figure 4:
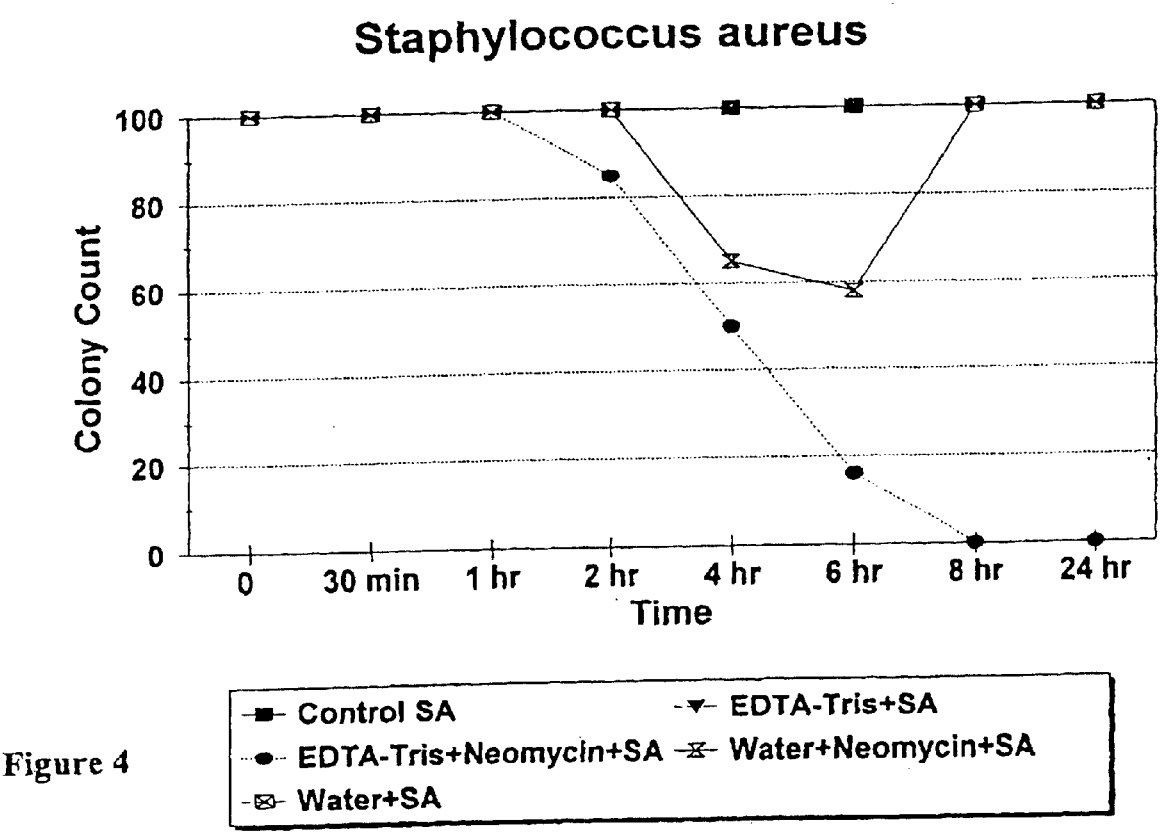
FIG. 4. Growth of *Staphylococcus aureus* on Mueller-Hinton agar when treated with combinations of EDTA, water, and neomycin.
Figure 5:
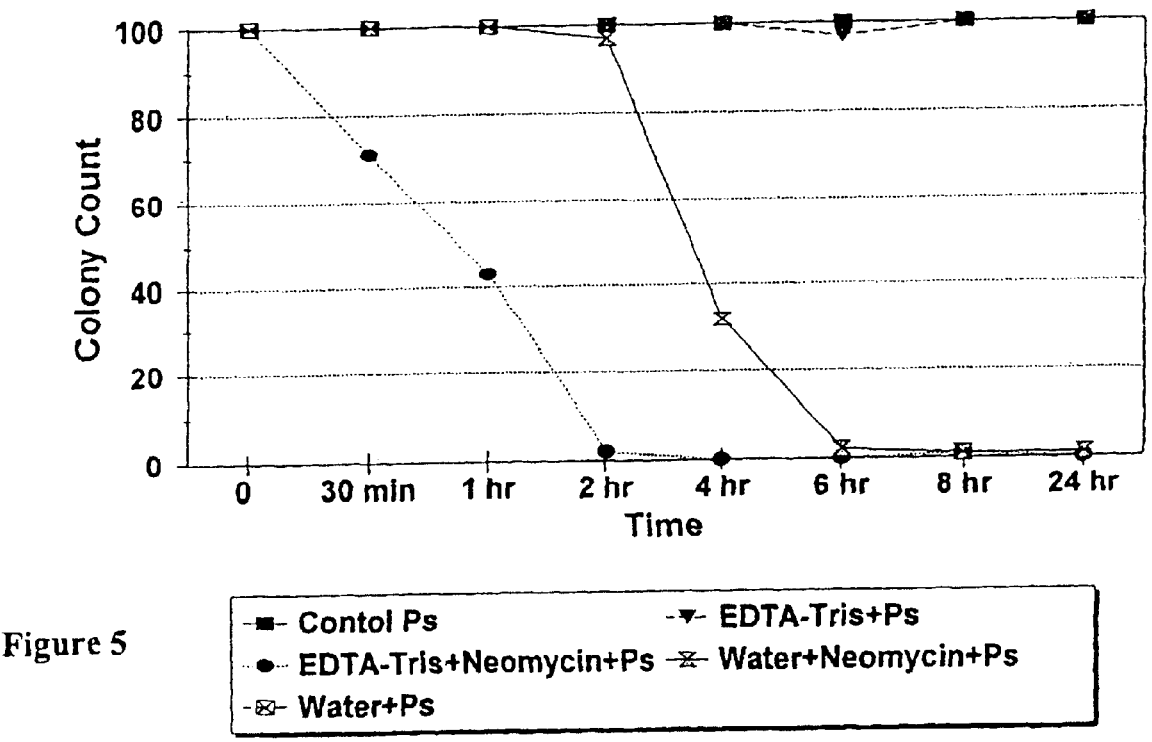
FIG. 5. Growth of *Pseudomonas aeruginosa* on Mueller-Hinton agar when treated alone or with combinations of EDTA, water, and neomycin.
Figure 6:
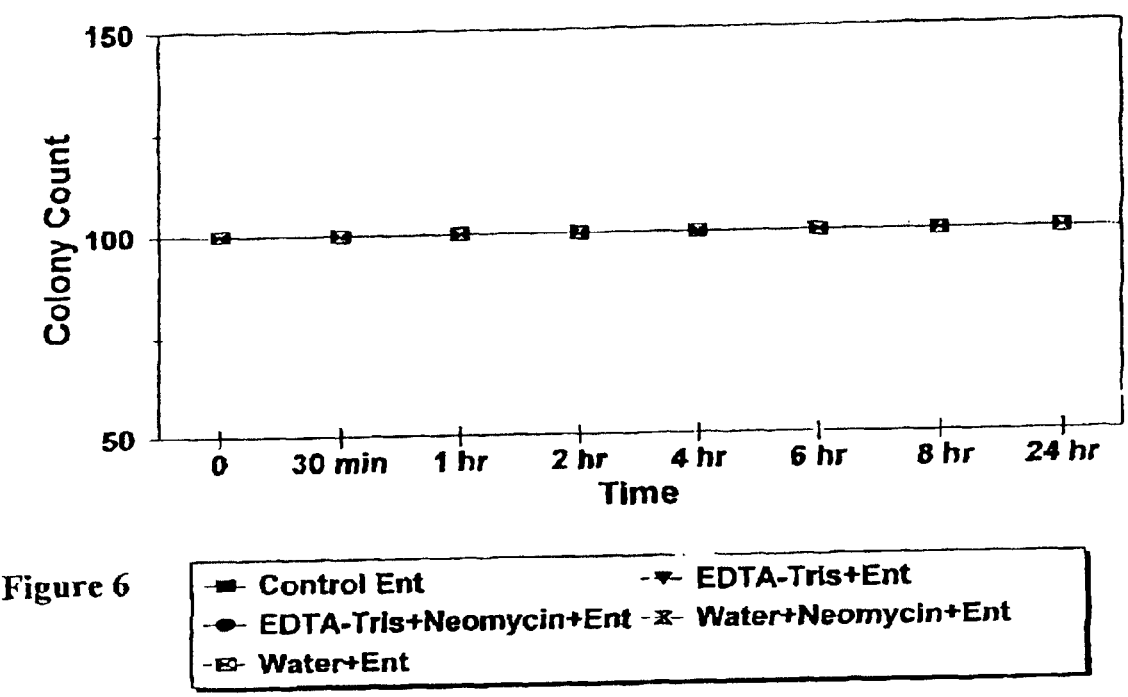
FIG. 6. Growth of *Enterococcus faecalis* on Mueller-Hinton agar when treated alone or with combinations of EDTA, water, and neomycin.

In the in vitro gauze-point-contactor study, the potentiation effect was seen for EDTA-Tris-neomycin reactions with *Ps. aeruginosa* and *Staph. aureus*. These reactions are illustrated in FIGS. 4–6. When the same combinations of EDTA-Tris and neomycin were reacted with *Ent. faecalis* no antibacterial activity was noted at these concentrations (FIG. 6).

EXAMPLE 9

FICs of Test Bacterial Strains and Chemical Disinfectants with EDTA

The MICs for solutions of EDTA-Tris and various disinfectants reacted with the test organisms are shown on Tables 5–6. FICs are given in Tables 7–9.

TABLE 5

Minimal inhibitory concentrations (MICs) of test organisms reacted with commercial chemical disinfectants or EDTA-Tris.

| | Organism | | | | |
|---|---|---|---|---|---|
| Chemicals | Bacillus sp. | *Staph. aureus* | *Ps. aeruginosa* | *P. mirabilis* | *E. coli* |
| EDTA-Tris | 0.125 | 0.25 | 1.25 | 2.50 | 2.50 |
| Glutracide (glutaraldehyde) | 0.50 | 2.00 | 2.50 | 2.50 | 2.50 |
| Magnaphen-100 (phenol and detergent) | 0.03 | 0.06 | 1.00 | 0.25 | 0.25 |
| BioSentry 904 (QAC) | 0.003 | 0.003 | 1.28 | 0.128 | 0.031 |
| Synergize (QAC and glutaraldehyde) | 0.0125 | 0.003 | 2.00 | 1.00 | 0.05 |
| Hydrogen peroxide | 0.05 | 0.02 | 0.09 | 0.19 | 0.12 |

MIC = dilution of stock solution.
[a]1 x stock solutions: EDTA-Tris, 5 mM EDTA + 50 mM Tris-HCl; Glutracide, 1:200; Magnaphen-100, 1:400; BioSentry 904, 1:256; Synergize, 1:256; hydrogen peroxide, 3%.

TABLE 6

Minimal inhibitory concentrations (MICs) of test organisms reacted with commercial chemical disinfectants or EDTA-Tris.

| | Organism | | | | |
|---|---|---|---|---|---|
| | | *S. typhimurium* | | | *S. enteritidis* |
| Chemical | Avian | DT104 | 6578 | TRC1 | |
| EDTA-Tris | 2.5 | 2.5 | 2.5 | 2.5 | 2.5 |
| Glutracide (glutaraldehyde) | 5.0 | 5.0 | 5.0 | 5.0 | 5.0 |
| Magnaphen-100 (phenol and detergent) | 0.33 | 0.33 | 0.33 | 0.33 | 0.25 |
| BioSentry 904 (QAC) | 0.026 | 0.026 | 0.026 | 0.026 | 0.026 |
| Synergize (QAC and glutaraldehyde) | 0.05 | 0.05 | 0.05 | 0.1 | 0.05 |
| Hydrogen peroxide | 0.005 | 0.005 | 0.005 | 0.005 | 0.005 |

MIC = dilution of stock solution.
[a]1 x stock solutions: EDTA-Tris, 5 mM EDTA + 50 mM TrisrHCl; Glutracide, 1:200; Magnaphen-100, 1:400; BioSentry 904, 1:256; Synergize, 1:256; hydrogen peroxide, 3%.
[c]avian = avian strain; DT104 = multiple antibiotic resistant strain; 6578 = parent strain; TRC1 = mar (multiple antibiotic and organic solvent resistance) mutant of *S. typhimurium* 65781.

Fractional inhibitory concentrations for EDTA-Tris disinfectant combinations (synergistic, additive, or antagonistic reactions) were determined for the test organisms. Solutions of EDTA-Tris potentiated (synergistic or additive) the antimicrobial effect of Magnaphen-100, BioSentry 904, Synergize, and hydrogen peroxide when reacted with most of the Gram-negative bacteria but did not react uniformly against the Gram-positive organisms. Reactions of EDTA-Tris and Glutracide were principally antagonistic in nature except with *Staph. aureus*, which was synergistic. Tables 3–5 summarize the results of this study.

TABLE 7

Fractional inhibitory concentrations (FICs) of various concentrations of chemical disinfectant and EDTA-Tris when reacted with Staph. aureus and E. coli strains V-I and Av.

| Chemical | Staph. aureus | E. coli V-1 | E. coli Av |
|---|---|---|---|
| Glutracide | 0.28[A] | 1.13[B] | 1.50[B] |
| Magnaphen-100 | 0.50[A] | 0.18[A] | 0.31[A] |
| BioSentry 904 | 0.56[C] | 0.38[A] | 0.38[A] |
| Syncrgize | 1.50[B] | 0.50[A] | 0.50[A] |
| Hydrogen peroxide | 1.48[B] | 0.53[C] | 0.50[A] |

[A]Synergistic reaction (FIC ~ 0.5).
[B]Antagonistic reaction (FIC > 1.0).
[C]Additive reaction (FIC > 0.5 to < 1.0).

TABLE 8

Fractional inhibitory concentrations (FICs) of various concentrations of chemical disinfectant and EDTA-Tris when reacted with test Salmonella organisms.

| | S. typhimurium | | | |
|---|---|---|---|---|
| Chemical | Avian | DT104 | 6578 | TRC1 |
| Glutracide | 1.5[B] | >2.0[B] | 1.5[B] | 1.5[B] |
| Magnaphen-100 | 0.75[C] | 0.58[C] | 0.5[D] | 0.75[C] |
| BioSentry 904 | 0.31[D] | 0.38[D] | 0.5[D] | 0.75[C] |
| Synergize | 0.5[D] | 0.31[D] | 0.5[D] | 0.63[C] |
| Hydrogen peroxide | 0.63[C] | 0.75[C] | 0.5[D] | 0.5[D] |

[A]Avian = avian strain; DTI04 = multiple antibiotic resistant strain; 6578 = parent strain; TRCI = mar (multiple antibiotic and organic solvent resistance) mutant S. typhimurium 65781.
[B]Antagonistic reaction (FIC > 1.0).
[C]Additive reaction (FIC :> 0.5 to < 1.0).
[D]Synergistic reaction (FIC <: 0.5).

TABLE 9

Fractional inhibitory concentrations (FICs) of various concentrations of chemical disinfectants and EDTA-Tris when reacted with test organisms.

| Chemical | P. mirabilis | Ps. aeruginosa | S. enteritidis | B subtilis |
|---|---|---|---|---|
| Glutracide | 1.5[A] | 1.0[B] | 1.5[A] | >2.0[A] |
| Magnaphen-100 | 0.56[B] | 0.28[C] | 0.31[C] | 1.0[A] |
| BioSentry 904 | 0.62[B] | 0.18[C] | 0.38[C] | >2.0[A] |
| Synergize | 0.37[C] | 0.18[C] | 0.5[C] | 0.49[C] |
| Hydrogen peroxide | 0.37[C] | 0.37[C] | 0.38[C] | 1.0[B] |

[A]Antagonistic reaction (FIC > 1.0).
[B]Additive reaction (FIC > 0.5 to < 1.0),
[C]Synergistic reaction (FIC < 0.5)

Resistant mutants did not develop when solutions of EDTA-Tris were reacted with *S. typhimurium, S. enteritidis,* an avirulent avian *E. coli,* a virulent avian *E. coli, B. subtilis, Staph. aureus.*

What is claimed is:

1. A method for administering an antimicrobial composition to an aquatic animal to inhibit the proliferation of a microbial infection or colonization, comprising the steps of:
    a) dissolving an antimicrobial composition in a carrier to give an antimicrobial solution, wherein the antimicrobial composition comprises at least one chelating agent and at least one antibiotic;
    b) immersing an aquatic animal in the antimicrobial solution;
    c) removing an aquatic animal from the antimicrobial solution; and
    d) placing an aquatic animal in water not containing the antimicrobial composition.

2. The method of claim 1, wherein the aquatic animal is selected from the group consisting of an aquatic mammal, an aquatic bird, a fish, an aquatic reptile, an amphibian, and an aquatic invertebrate.

3. The method of claim 1, wherein the aquatic animal is a fish.

4. The method of claim 3, wherein the fish is an ornamental fish.

5. The method of claim 3, wherein the fish is a farmed fish.

6. The method of claim 1, wherein the aquatic animal has a microbial infection.

7. The method of claim 6, wherein the microbial infection is a bacterial infection.

8. The method of claim 7, wherein the bacterial infection is a Gram-negative bacteria selected from the genera Aeromonas, Pseudomonas, Escherichia, Yersinia, Vibrio, Flexibacter, Nocardia, Flavobacterium, Edwardsiella, and Cytophagia.

9. The method of claim 7, wherein the microbial infection is a Gram-positive bacteria selected from the genera Bacillus, Staphylococcus, Streptococcus, Mycobacterium and Renibacterium.

10. The method of claim 1, wherein the chelating agent is selected from ethylenediamenetetracetic acid (EDTA), triethylene tetramine dihydrochloride (TRIEN), ethylene glycol-bis (β-aminoethyl ether)-N, N, N', N'-tetracetic acid (EGTA), diethylenetriamin-pentaacetic acid (DPTA), triethylenetetramine hexaacetic acid (TTG), deferoxamine, Dimercaprol, edetate calcium disodium, zinc citrate, penicilamine succimer and Editronate.

11. The method of claim 1, wherein the chelating agent is further selected from ethylenediamenetetracetic acid (EDTA), triethylene tetramine dihydrochloride (TRIEN), ethylene glycol-bis (β-aminoethyl ether)-N, N, N', N'-tetracetic acid (EGTA), diethylenetriamin-pentaacetic acid (DPTA), and triethylenetetramine hexaacetic acid (TTG).

12. The method of claim 1, wherein the chelating agent is ethylenediamenetetracetic acid (EDTA) or triethylene tetramine dihydrochloride (TRIEN).

13. The method of claim 1, wherein the chelating agent in solution has a concentration in the solution of between about 0.1 mM and about 50 mM.

14. The method of claim 1, wherein the chelating agent in solution has a concentration in the solution of between about 0.1 mM and about 10 mM.

15. The method of claim 1, further comprising the step of adding a pH buffering agent to the antimicrobial solution.

16. The method of claim 15, wherein the pH buffering agent is Tris (hydroxymethyl) aminomethane (TRIZMA Base).

17. The method of claim 15, wherein the pH buffering agent has a concentration in the antimicrobial solution of between about 10 mM and about 100 mM.

18. The method of claim 15, wherein the pH buffering agent has a concentration in the antimicrobial solution of about 50 mM.

19. The method of claim 15, wherein the pH of the antimicrobial solution is in the range of about 7.0 to about 9.0.

20. The method of claim 15, wherein the pH of the antimicrobial solution is about 8.0.

21. The method of claim 1, wherein the antibiotic is biologically active against a bacterial species and is selected from the group consisting of a β-lactam, an aminoglycoside, a vancomycin, a bacitracin, a macrolide, an erythromycin, a lincosamide, a chloramphenicol, a tetracycline, a gentamicin, an amphotericin, a cefazolin, a clindamycin, a mupirocin, a nalidixic acid, a sulfonamide and trimethoprim, a streptomycin, a rifampicin, a metronidazole, a quinolone, a novobiocin, a polymixin or a gramicidin.

22. The method of claim 21, wherein the antibiotic is further selected from the group consisting of a penicillin, an aminoglycoside; a vancomycin, a chloramphenicol, an erythromycin, a tetracycline, gentamicin, nalidixic acid; and a streptomycin.

23. The method of claim 22, wherein the tetracycline is oxytetracycline.

24. The method of claim 22, wherein the antibiotic is selected from neomycin, amikacin, and gentamicin.

25. The method of claim 22, wherein the antibiotic is neomycin.

26. The method of claim 1, wherein the antibiotic is biologically active against Gram-negative bacteria.

27. The method of claim 1, wherein the antimicrobial composition is biologically active against a Gram-positive bacterium.

28. A method for administering an antimicrobial composition to an aquatic animal to inhibit the proliferation of a microbial infection, comprising the steps of:
   a) identifying an aquatic animal having a microbial infection;
   b) providing an antimicrobial solution comprising at least one chelating agent, wherein the chelating agent is EDTA, at least one antibiotic biologically active against a microbial infection, and a carrier;
   c) optionally adding a pH buffering agent to the antimicrobial solution;
   d) adjusting the pH of the antimicrobial solution to a value of between about 7.0 and about 9.0;
   e) contacting the aquatic animal with the antimicrobial solution;
   f) removing the animal from the antimicrobial solution; and
   g) repeating steps e) and f) providing that the microbial infection is not eliminated from the antimicrobial animal by steps a)–f).

29. The method of claim 28, further comprising the steps of:
   (a) identifying the microbial infection;
   (b) identifying an antibiotic capable of inhibiting the proliferation of the microbial infection;
   (c) determining the MIC and FIC for the antibiotic and a chelating agent; and
   (d) adjusting the concentration of the antibiotic and the chelating agent to inhibit the proliferation of the microbial infection.

30. The method of claim 28, wherein the animal is an aquatic animal selected from the group consisting of an aquatic mammal, an aquatic bird, a fish, an aquatic reptile, an amphibian, and an aquatic invertebrate.

31. The method of claim 28, wherein the aquatic animal is a fish.

32. The method of claim 28, wherein the fish is an ornamental fish.

33. The method of claim 28, wherein the fish is a farmed fish.

34. A kit for use in administering an antibiotic to an aquatic animal for inhibiting the proliferation of a microbial infection of the animal, comprising:
   at least one container having therein at least one chelating agent, and optionally at least one antibiotic; and packaging material, wherein the packaging material comprises instructions directing the use of the kit for administering the antibiotic and chelating agent to inhibit the proliferation of a microbial infection of an aquatic animal.

35. A kit as in claim 34, further comprising a pH buffering agent and instructions for the use thereof, to enhance the antimicrobial activity of the at least one antibiotic for inhibiting the proliferation of a microbial infection of an aquatic animal.

* * * * *